United States Patent
Gigan et al.

(10) Patent No.: US 9,874,502 B2
(45) Date of Patent: Jan. 23, 2018

(54) METHODS AND DEVICE FOR TRAPPING, MOVING AND SORTING PARTICLES CONTAINED IN A FLUID

(71) Applicant: FONDS DE L'ESPCI-GEORGES CHARPAK, Paris (FR)

(72) Inventors: Sylvain Gigan, Paris (FR); Giorgio Volpe, Paris (FR); Giovanni Volpe, Ankara (TR)

(73) Assignee: Fonds De L'espci-Georges Charpak, Paris (FR)

( * ) Notice: Subject to any disclaimer, the term of this patent is extended or adjusted under 35 U.S.C. 154(b) by 167 days.

(21) Appl. No.: 14/758,911

(22) PCT Filed: Dec. 30, 2013

(86) PCT No.: PCT/FR2013/053278
§ 371 (c)(1),
(2) Date: Jul. 1, 2015

(87) PCT Pub. No.: WO2014/106715
PCT Pub. Date: Jul. 10, 2014

(65) Prior Publication Data
US 2015/0338324 A1 Nov. 26, 2015

(30) Foreign Application Priority Data
Jan. 2, 2013 (FR) ...................... 13 50015

(51) Int. Cl.
*G01N 1/40* (2006.01)
*G02B 5/02* (2006.01)
*B01L 3/00* (2006.01)
*G01N 21/49* (2006.01)
*G01N 21/85* (2006.01)

(52) U.S. Cl.
CPC ...... *G01N 1/4077* (2013.01); *B01L 3/502761* (2013.01); *G01N 21/49* (2013.01);
(Continued)

(58) Field of Classification Search
CPC ...... G01N 1/4077; G01N 21/47; G01N 21/49; G01N 21/85; G02B 5/0273; B01L 2400/0454; B01L 3/502761
(Continued)

(56) References Cited

U.S. PATENT DOCUMENTS 5,212,382 A * 5/1993 Sasaki .................. H05H 3/04
250/251
6,055,106 A * 4/2000 Grier .................... G02B 21/32
359/15

(Continued)

OTHER PUBLICATIONS

Shvedov et al. International Symposium on High Power Laser Ablation, 2010, pp. 26-37.*

(Continued)

Primary Examiner — Maureen Wallenhorst
(74) Attorney, Agent, or Firm — Miller, Matthias & Hull LLP

(57) ABSTRACT

The invention relates to a method for trapping particles contained in a fluid including at least the steps of generating a coherent light beam, diffusing the coherent light beam using a passive diffusive element to yield a diffused beam having a field of optical speckles, and causing the diffused beam to interact with a plurality of particles contained in a fluid.

20 Claims, 3 Drawing Sheets

(52) U.S. Cl.
CPC .... G02B 5/0273 (2013.01); B01L 2400/0454 (2013.01); G01N 21/85 (2013.01)

(58) Field of Classification Search
USPC .......... 436/164, 180; 422/82.05, 82.09, 502; 250/251; 435/5, 29, 287.1
See application file for complete search history.

(56) References Cited

U.S. PATENT DOCUMENTS

| | | | | |
|---|---|---|---|---|
| 6,061,133 | A * | 5/2000 | Freischlad | G01B 9/0209 356/460 |
| 6,159,749 | A * | 12/2000 | Liu | B01L 3/502 250/251 |
| 7,732,758 | B2 * | 6/2010 | Dholakia | G21K 1/006 209/129 |

OTHER PUBLICATIONS

Staforelli et al. Optics Communications, vol. 283, 2010, pp. 4722-4726.*

International Search Report for related International Application No. PCT/FR2013/053278; dated Apr. 10, 2014.
D. Boiron et al; "*Trapping and cooling cesium atoms in a speckle field*"; The European Physical Journal D; vol. 7, No. 3' Jan. 1, 1999; p. 373.
A. Lencina et al; *Three-dimensional clustered speckle fields: theory, simulations and experimental verification*; Optics Express; vol. 20, No. 19; Sep. 10, 2012; p. 21145.
Vladlen G. Shvedov et al.; "*Selective Trapping of multiple particles by volume speckle field*"; Optics Express; vol. 18, No. 3; Feb. 1, 2010; p. 3137.
Shvedov et al; *Multiple trapping with optical bottle beam*; http://www.opticsinfobase.org, 2009.
J. Lye et al: Bose-Einstein Condensate in a Random Potential; Physical Review Letters; vol. 95, No. 7; Aug. 1, 2005; p. 070401.
Jean-Marc R. Fournier et al; "*Building optical matter with binding and trapping forces, proceedings of spie*"; vol. 5514; Oct. 18, 2004; pp. 308-317.
Celment D et al: "*Experimental study of the transport of coherent interacting matter-waves in a 1D random potential induced by laser speckle*"; New Journal of Physics, Institute of Physics Publishing, Bristol, GB; vol. 8, No. 8; Aug. 1, 2006; p. 165.

* cited by examiner

METHODS AND DEVICE FOR TRAPPING, MOVING AND SORTING PARTICLES CONTAINED IN A FLUID

CROSS-REFERENCE TO RELATED APPLICATIONS

This application is a 35 USC § 371 U.S. national stage filing of International Patent Application No. PCT/FR2013/053278 filed on Dec. 30, 2013, which claims priority under the Paris Convention and 35 USC § 119 to French Patent Application No. 13 50015, filed on Jan. 2, 2013.

FIELD OF THE DISCLOSURE

The present invention relates to methods and devices for trapping, moving, and sorting particles contained in a fluid.

BACKGROUND OF THE DISCLOSURE

The technical field of the invention is that of methods and devices for manipulating dielectric or metal microparticles or nanoparticles, or organic particles such as molecules, microorganisms, or viruses.

These methods and devices are used, for example, in microfluidic devices or in labs-on-a-chip for analysis or chemical or biological synthesis applications.

Methods for trapping and moving particles in a fluid are known from the prior art and are commonly called "optical tweezers."

These methods use a focused laser beam to trap and manipulate a particle contained in a fluid.

The refraction of light at the interface between the particle and the surrounding fluid exerts a force on the particle, a function of the difference in refractive index between the particle and the fluid, which allows manipulating the particle (for example see Ashkin et al., Optics Letters Vol. 11, p 288 (1986)).

The force exerted on the particle is a function of the electric field gradient of the laser which displaces the particle toward the most intense area of illumination in the center of the focused beam, the focal area of the focused laser beam thus constituting an "optical trap."

Document U.S. Pat. No. 7,732,758 B2 describes an example of such an optical trap in which a focused laser allows holding, manipulating, and moving a particle in a fluid.

The force exerted by the laser beam on a particle is particularly dependent on the composition and size of the particles. It is therefore possible to sort particles according to these parameters, and there is a need for devices for trapping, moving, and sorting particles that can trap, move, and sort a large number of particles for the microfluidic and lab-on-a-chip applications mentioned above.

The device described in U.S. Pat. No. 7,732,758 B2 has the disadvantage of using one laser generator per optical trap and thus only allows trapping and manipulating a small number of particles unless a device of great complexity and size is implemented.

Document U.S. Pat. No. 7,973,275 B2 describes an example of a method for trapping and moving particles that manipulates particles by means of multiple optical traps generated by a single laser source.

This device, however, requires the use of an active optical element controlled by a computer in order to generate a hologram. The presence of such an active optical element makes such devices expensive and complex to use. In addition, the determination of the holographic figure to be projected requires significant computing power, and some optical trap configurations are impossible to generate.

The present invention is intended to overcome these disadvantages.

SUMMARY OF THE DISCLOSURE

A description of the invention as characterized in the claims is provided below.

According to a first aspect, the invention relates to a method for trapping particles contained in a fluid, comprising at least the steps of:
  generating a coherent light beam,
  scattering the coherent light beam by means of a passive diffusive element in order to yield a scattered beam having an optical speckle field,
  causing the scattered beam to interact with a plurality of particles contained in a fluid.

With these arrangements, it is possible to generate an optical field having a large number of optical traps. The method employs a passive diffusive element that is inexpensive, portable, and easy to manufacture and use. The quality of the optical traps generated is not dependent on the resolution and type of the diffusive element used. A wide variety of particles can be trapped by the optical field generated. The particle trapping can occur over a wide area.

In preferred embodiments of the invention, one or more of the following arrangements may possibly be used:
  the passive diffusive element scatters the coherent light beam into a scattered beam capable of having a speckle contrast ratio substantially greater than fifty percent;
  the scattering step comprises reflection or transmission of the coherent light beam by the passive diffusive element to yield the scattered beam;
  the passive diffusive element is one of: a rough surface, or a multi-mode optical fiber, or a multi-scattering medium, in particular a medium comprising an amorphous material, a translucent material, a nano-structured material, or a biological material;
  the diffusive element is a rough internal or external surface of a passage containing the fluid;
  the rough surface comprises rough areas of dimensions substantially near a wavelength of the coherent light beam;
  the coherent light beam is generated such that a wavelength of said beam is substantially equal to a wavelength of electromagnetic radiation at which the particles are transparent;
  the particles have an average diameter of between 1 nanometer and 0.1 millimeters;
  the particles are either: dielectric or metal microparticles or nanoparticles; or organic nanoparticles or microparticles, in particular molecules or parts of molecules, microorganisms or parts of microorganisms, and viruses or parts of viruses.

The invention also relates to a method for moving particles contained in a fluid, comprising the steps of a method for trapping particles as described above, the method for moving particles further comprising a step of modifying the optical speckle field of the scattered beam.

In preferred embodiments of the invention, the step of modifying the optical speckle field of the scattered beam may comprise modifying the coherent light beam, in particular moving the coherent light beam or modifying a wavefront of the coherent light beam before it is scattered to yield a scattered beam.

The invention also relates to a method for sorting particles contained in a fluid, comprising the steps of a method for trapping particles as described above or the steps of a method for moving particles as described above, the method for sorting particles further comprising a step of collecting particles to be collected among the plurality of particles after said particles to be collected have interacted with the scattered beam.

In preferred embodiments of the invention, the plurality of particles may comprise at least one particle of a first type and at least one particle of a second type, said at least one particle of a first type and said at least one particle of a second type differing in their composition or their size, the particles to be collected being said at least one particle of the first type.

In another aspect, the invention relates to a device for trapping particles contained in a fluid, comprising:
 a means of generating a coherent light beam,
  a passive diffusive element capable of scattering the coherent light beam to yield a scattered beam having an optical speckle field, the scattered beam being capable of interacting with a plurality of particles contained in a fluid.

According to yet another aspect, the invention provides a device for moving particles contained in a fluid, comprising a means of generating a coherent light beam, a passive diffusive element capable of scattering the coherent light beam to yield a scattered beam having an optical speckle field, the scattered beam being capable of interacting with a plurality of particles contained in a fluid, and a means of modifying the optical speckle field of the scattered beam.

Finally, the invention relates to a device for sorting particles contained in a fluid, comprising a means of generating a coherent light beam, a passive diffusive element capable of scattering the coherent light beam to yield a scattered beam having an optical speckle field, the scattered beam being capable of interacting with a plurality of particles contained in a fluid, and a means of collecting particles to be collected among the plurality of particles after said particles to be collected have interacted with the scattered beam.

Other features and advantages of the invention will become apparent from the following description of several of its embodiments, given by way of non-limiting examples, with reference to the accompanying drawings.

BRIEF DESCRIPTION OF THE DRAWINGS

In the drawings.

In the various figures, the same references designate identical or similar elements.

DETAILED DESCRIPTION OF THE DISCLOSURE

Figure 1:
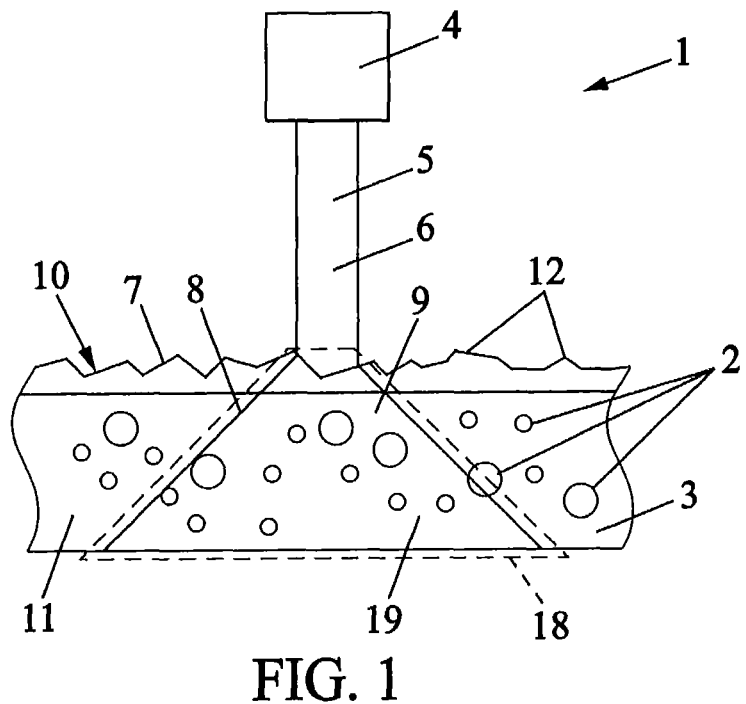
FIG. 1 is a schematic view of a device for trapping particles contained in a fluid according to a first embodiment of the invention.

Referring to FIG. 1, a device 1 for trapping particles 2 contained in a fluid 3 is shown.

This device 1 implements the steps of a method for trapping particles 2 contained in a fluid 3 according to one embodiment of the invention.

The fluid 3 may be any more or less viscous fluid, for example water, liquid, gel, or even a gas, for example air.

The particles 2 may be dielectric or metallic nanoparticles or microparticles.

The particles 2 may be organic nanoparticles or microparticles, in particular molecules or parts of molecules, microorganisms or parts of microorganisms, and viruses or parts of viruses.

The fluid 3 may then be, for example, an organic fluid or even living tissue.

The particles have an average diameter of between 1 nm and 0.1 mm and therefore are nanoparticles or microparticles.

The particles may be non-spherical in shape, the average diameter of a particle being understood to be a diameter averaged over the surface of said particle.

This trapping device 1 firstly comprises a means of generating 4 a coherent light beam 5, and a trapping method of the invention comprises a step of generating 4 a coherent light beam 5.

The coherent light beam 5 is, for example, a laser beam, and the generating means 4 is a laser source, for example a laser diode or a laser generator of any known type, for example a crystal, liquid, or gas laser.

The coherent light beam 5 may comprise wavelengths 6 of electromagnetic radiation that lie within any spectral range.

In one embodiment, the coherent light beam 5 may include wavelengths 6 in the visible or infrared range.

In one embodiment, the coherent light beam 5 may include wavelengths 6 where the particles 2 are substantially transparent.

In this manner, the coherent light beam 5 does not heat the particles 2 too much, which could damage them, for example when said particles are organic particles.

In one embodiment, the coherent light beam 5 is not focused, meaning it is defocused or collimated.

This allows trapping particles over a large area.

The trapping device 1 further comprises a passive diffusive element 7 capable of scattering the coherent light beam 5 to yield a scattered beam 8 having an optical speckle field 9, and the method for trapping particles includes a step of scattering the coherent light beam 5 by means of a passive diffusive element 7 to yield a scattered beam 8 having an optical speckle field 9.

In a first embodiment of the invention illustrated in FIG. 1, the passive diffusive element has a rough surface 10.

In the example of FIG. 1, the rough surface 10 is a surface of a passage 11 containing the fluid 3.

The rough surface 10 may be an inner or outer surface of said passage 11 containing the fluid 3, meaning a surface in contact with the fluid 3 or an outwardly facing surface of said passage.

It is also possible for the rough surface 10 to be housed within the thickness of the passage 11 wall.

The passive diffusive element 7 is adapted to scatter the coherent light beam 5 significantly, meaning that the scattered beam 8 has a significant optical speckle field 9.

The rough surface 10 may therefore comprise for example rough areas 12 of substantially similar dimensions, or of the same order of magnitude, as a wavelength 6 of the coherent light beam 5.

In this manner, the rough areas 12 will induce differences in step, and thus phase differences, between the waves of the coherent light beam 5 scattered at different locations on the rough surface 10.

These phase differences will cause constructive or destructive interference in the scattered beam 8 and thus an optical speckle field 9 (for example see J W Goodman, Some fundamental properties of speckle, J. Opt. Soc. Am. 66 (11), 1145-1150 (1976).

As the scattered beam 8 has an optical speckle field 9, it presents a plurality of areas of constructive interference 20 and destructive interference 21 where the electric field of the scattered beam 8 is maximal or minimal.

The optical speckle field 9 of the scattered beam 8 is an extended speckle field, meaning that it is not restricted to a single area of constructive interference 20 or destructive interference 21 of high intensity, or to a limited number of such areas, but contains a large number of areas of constructive interference 20 and destructive interference 21 and of high intensity (high intensity is understood to mean, for example, an intensity greater than ten percent of the average intensity of the scattered beam 8 in the fluid).

In particular, the scattered beam 8 can thus be suitable for providing a speckle contrast ratio substantially greater than fifty percent.

In one embodiment, the speckle contrast ratio may be substantially greater than seventy-five percent.

The speckle contrast ratio is measured for example as follows:

The speckle contrast can be measured simply, for example by the following operations.

A camera operating in the frequency range of the coherent light beam is placed in the scattered light field, for example substantially where there is fluid.

An image is then captured of the speckle field in the general area of the fluid, meaning in the speckle field substantially affecting the particles.

"Image of the speckle field" is understood to mean that the set of pixels in the image captured by the camera provides an intensity distribution which reflects the intensity distribution of the speckle field at the camera.

A speckle contrast ratio can then be determined from the image by calculating the contrast in the intensity of the set of pixels in the image captured by the camera.

The speckle contrast is thus calculated as being, for example, the ratio between the standard deviation of all pixels in the image and the average intensity of all pixels in the image.

The speckle contrast is especially a function of the surface area of the image captured by the camera (in other words the surface area of the speckle field captured by the camera sensor), and the scattered beam 8 can, for example, be adapted to present a speckle contrast ratio substantially greater than fifty percent for a surface area of the image captured by the camera that is greater than 1 square micrometer.

Figure 2:
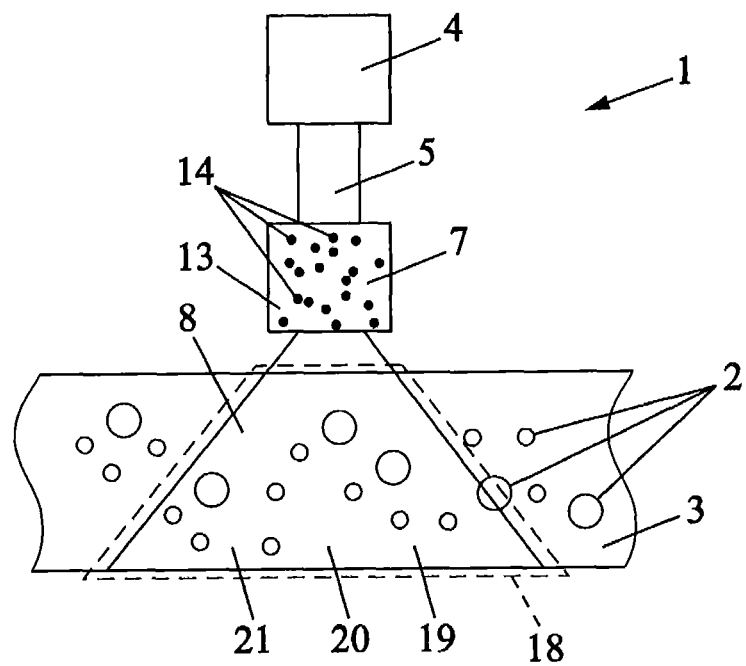
FIG. 2 is a schematic view of a device for trapping particles contained in a fluid according to a second embodiment of the invention.
Figure 3:
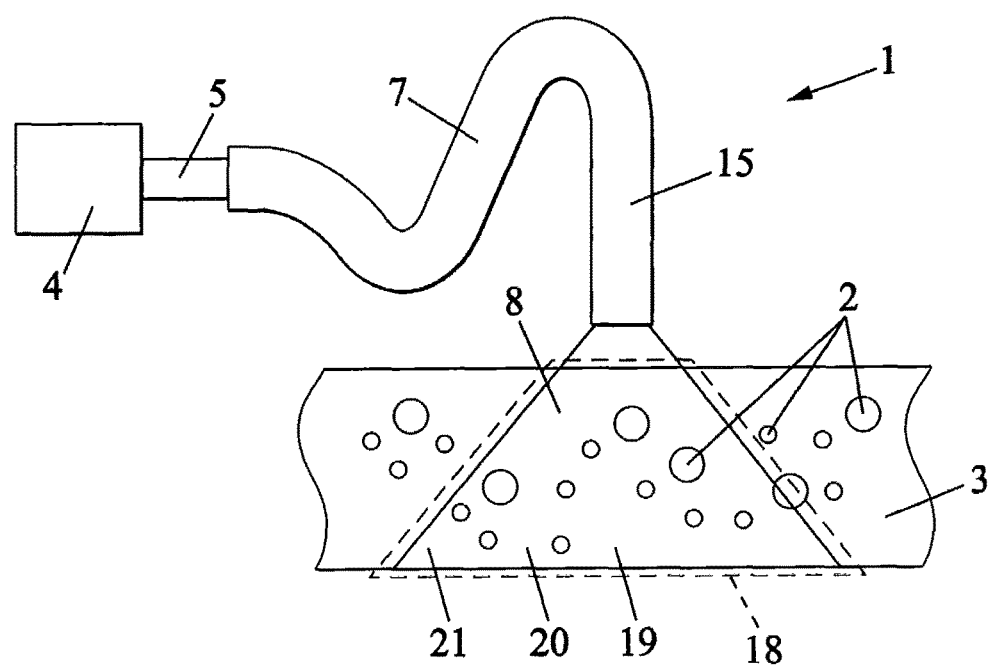
FIG. 3 is a schematic view of a device for trapping particles contained in a fluid according to a third embodiment of the invention.
Figure 4:
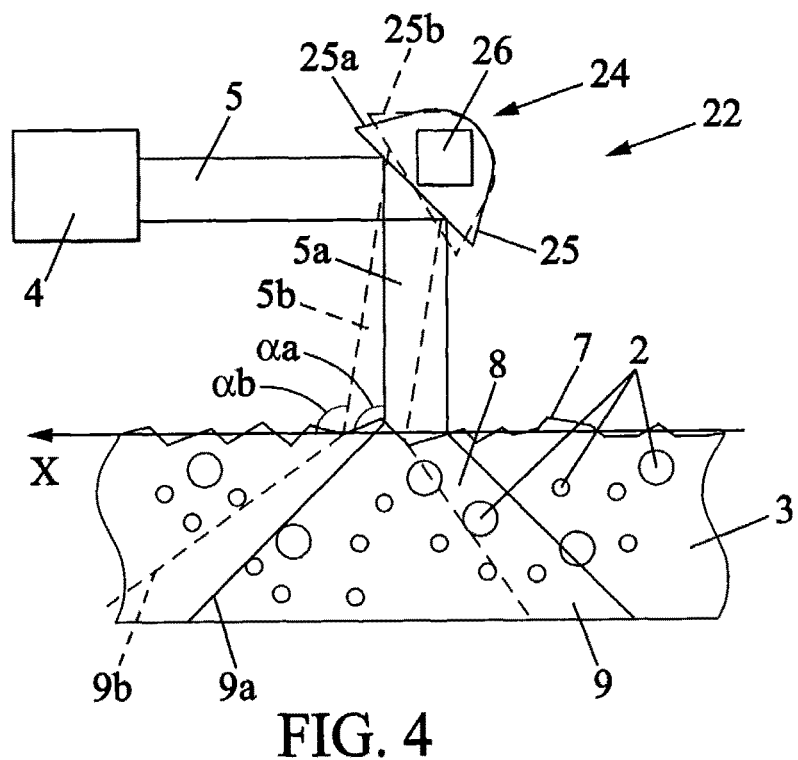
FIG. 4 is a schematic view of a device for moving particles contained in a fluid according to one embodiment of the invention.

In other embodiments, illustrated in FIGS. 2, 3 and 4, the passive diffusive element 7 may be varied and the scattering achieved by the passive diffusive element 7 may in particular comprise a reflection or transmission of the coherent light beam by the passive diffusive element 7 to yield the scattered beam 8.

The passive diffusive element 7 is passive, meaning that it requires no energy supply and has no electronics or active components such as piezoelectric components or liquid crystals.

In the example of FIG. 2, the passive diffusive element 7 thus comprises a multi-scattering medium 13, for example a medium comprising an amorphous material, a translucent material, a nano-structured material, or a biological material.

When the coherent light beam 5 passes through such a multi-scattering medium 13, the beam is scattered significantly, meaning that it is deflected in many different directions by interactions with a plurality of optical diffusers 14.

The optical diffusers 14 may be inhomogeneities of any type, as long as they scatter at least one wavelength 6 of the coherent light beam 5.

Thus, by way of example, in an amorphous material, the optical diffuser 14 may be grain boundaries, pigments, irregularities of the material; in a translucent material the optical diffusers 14 may be impurities or irregularities.

In a nano-structured material, the optical diffusers 14 may be irregularities produced by known micro- or nano-fabrication methods.

Finally, in a biological material, optical diffusers 14 are naturally present due to the high level of inhomogeneities in biological materials.

The multi-scattering medium 13 may thus include living tissue, such as animal skin in which the cells and internal elements constitute optical diffusers 14.

In the example of FIG. 3, the passive diffusive element 7 comprises a multi-mode optical fiber 15.

Propagation of the coherent light beam 5 in the multi-mode optical fiber 15 generates multiple reflections which allow scattering the coherent light beam 5 into a scattered beam 8.

In yet another embodiment of the passive diffusive element 7, said element may comprise a mirror that scatters light, for example by means of rough areas substantially similar to the rough areas 12 described above in relation to the rough surface 10.

Thus, the rough areas of the mirror may be of dimensions substantially similar to, or of the same order of magnitude as, a wavelength 6 of the coherent light beam 5.

In one embodiment of the invention, the passive diffusive element 7 is a linear medium, meaning that the wavelengths 19 of the scattered beam 8 are identical to the wavelengths 6 of the coherent light beam 5.

In one embodiment, the passive diffusive element 7 and the coherent light beam 5 are such that the scattered beam 8 is not focused, meaning that it is defocused or collimated.

This allows trapping particles over a large area.

A method according to the invention further comprises a step in which the scattered beam 8 interacts with a plurality of particles 2 of a fluid 3 contained in an interaction region 18.

As described above, refraction of the scattered beam 8 at the interface between a particle 2 and the surrounding fluid 3 exerts a force on said particle 2 which is in particular a function of the difference in refractive index between the particle 2 and the fluid 3.

The force exerted on the particle 2 is also a function of the electric field gradient of the scattered beam 8.

The plurality of areas of constructive 20 and destructive 21 interference thus constitutes a plurality of "optical traps" of different trapping "depth" and of known size.

In particular, if the refractive index of the fluid is lower than the refractive index of the particle 2, the particle will become trapped in an area of constructive interference 20.

Conversely, if the refractive index of the fluid is higher than the refractive index of the particle 2, the particle will be pushed toward an area of destructive interference 21.

The term trap is understood here to mean the action of a force on the particle 2, tending to move the particle 2 toward an area of constructive 20 or destructive 21 interference.

Thus, in particular if the fluid 3 is in motion relative to the scattered beam 8, the force exerted on a particle 2 may not be sufficiently strong to immobilize said particle 2 but may be sufficient to change the motion of the particle 2, in particular slowing it, as detailed below in relation to devices and methods for moving 22 or sorting 23 particles 2 according to the invention.

The force exerted by the scattered beam 8 on a particle 2 is dependent on the refractive index of the particle 2 but also on other parameters, including the size of the particle 2.

The particles 2 are therefore trapped more or less securely depending on said parameters, making it possible to sort them as will be further detailed below in relation to devices and methods for moving 22 and sorting 23 particles 2.

Referring to FIG. 4, a device for moving 22 particles 2 contained in a fluid 3 comprises the elements of a device for trapping 1 particles 2 as described above and in particular a means of generating 4 a coherent light beam 5 and a passive diffusive element 7 capable of scattering the coherent light beam 5 to yield a scattered beam 8 having an optical speckle field 9, the scattered beam 8 being capable of interacting with a plurality of particles 2 contained in a fluid 3.

Similarly, a method for moving particles 2 contained in a fluid 3 comprises the steps of a method for trapping particles 2 as described above.

The device for moving 22 particles 2 further comprises a means of modifying 24 the optical speckle field 9 of the scattered beam 8 and the method for moving particles 2 comprises a step of modifying the optical speckle field 9 of the scattered beam 8.

In the example of FIG. 4, the means of modifying 24 the optical speckle field 9 comprises a rotating mirror 25 which reflects the coherent light beam 5 before said beam is scattered by the passive diffusive element 7.

The rotating mirror 25 is rotated by a rotation actuator 26.

When the rotation actuator 26 rotates the rotating mirror 25 from position 25a to position 25b, the angle α at which the coherent light beam 5 reaches the passive diffusive element 7 varies from angle αa to angle αb.

If the difference between angles αa and αb is small, the optical speckle field 9 moves from position 9a to position 9b, in a movement direction X, without the areas of constructive interference 20 and destructive interference 21 being significantly altered (for example see I. Freund and M. Rosenbluh, Memory effects in propagation of optical waves through disordered media, Phys. Rev. Lett. 61, 2328-2331 (1988)).

The particles 2 that are trapped in the areas of constructive interference 20 and/or destructive interference 21 then move with the optical speckle field 9 from positions 2a to positions 2b.

The range of possible movement between positions 9a and 9b depends in particular on the characteristics of the coherent light beam 5 and of the passive diffusive element 7.

The optical speckle field 9 can thus be moved a fraction of a micrometer to several tens of micrometers or more, depending on the characteristics of the laser and the scattering medium.

By repeating multiple times the step of modifying the optical speckle field 9 of the scattered beam 8, on average the particles 2 are thus moved in the movement direction X.

Other ways of modifying the optical speckle field 9 of the scattered beam 8 are possible.

For example, the rotating mirror 25 may be replaced by, or used in conjunction with, a translating mirror moving along a translation axis and actuated by a linear actuator.

According to another variant, the coherent light beam 5 can be modified, for example by means of a spatial light modulator (or SLM) which, for example, modifies the wavefront of the coherent light beam 5.

Alternatively, the optical speckle field 9 of the scattered beam 8 may be modified by movement of the passive diffusive element 7, for example a translation and/or rotation of said passive diffusive element 7 by means of an actuator.

It is also possible to modify the optical speckle field 9 of the scattered beam 8 by moving the means of generating 4 the coherent light beam 5, by translation and/or rotation of said generating means 4, for example the laser source when said generating means 4 is a laser source, by means of an actuator.

Figure 5A:
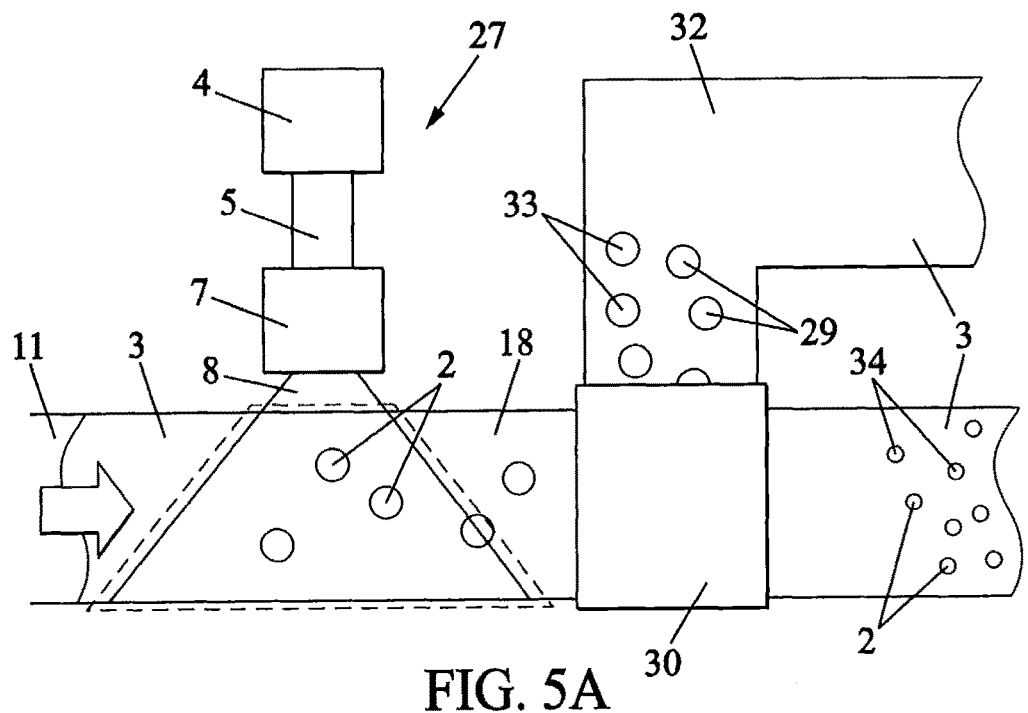
FIG. 5a is a schematic view of a device for sorting particles contained in a fluid according to a first embodiment of the invention.

Referring now to FIG. 5a, a device for sorting 27 particles 2 contained in a fluid 3 comprises, in a first embodiment, the elements of a device for trapping 1 particles 2 as described above and in particular a means of generating 4 a coherent light beam 5, and a passive diffusive element 7 capable of scattering the coherent light beam 5 to yield a scattered beam 8 having an optical speckle field 9, the scattered beam 8 being suitable for interacting with a plurality of particles 2 contained in a fluid 3.

Similarly, a method for sorting particles 2 contained in a fluid 3 comprises the steps of a method for trapping particles 2 as described above.

The device for sorting 27 particles 2 further comprises a means of collecting 28 particles to be collected 29 among the plurality of particles 2 after said particles to be collected 29 have interacted with the scattered beam 8, and the method for sorting particles 2 contained in a fluid 3 comprises a step of collecting 28 the particles to be collected 29 among the plurality of particles 2 after said particles to be collected 29 have interacted with the scattered beam 8.

In a first embodiment of a device and a method for sorting 27 particles 2, the collecting means 28 may be a valve 30 with its inlet connected to passage 11 and its outlet to a first outlet passage 31 and a second outlet passage 32.

The fluid 3 containing the particles 2 is set in motion so that it is first located in the region of interaction 18 with the scattered beam 8 and then reaches the collecting means 28.

Initially, the valve 30 can be placed in a first position where it allows the fluid 3 entering by passage 11 to exit into the first outlet passage 31.

After a predetermined time t1, the valve 30 can be placed in a second position where it allows the fluid 3 entering by passage 11 to exit into the second outlet passage 32.

The force exerted on a particle 2 by the scattered beam 8 is dependent on the refractive index of the particle 2 as well as on other parameters, including the size of the particle 2.

The particles 2 are therefore trapped more or less securely within the interaction region 18 by the beam 8, and will reach the collecting means 28 more or less quickly depending in particular on their refractive index, size, composition, and shape.

More specifically, the plurality of particles 2 may comprise at least one particle 33 of a first type and at least one particle 34 of a second type.

The first type of particle and the second type of particle differ in their refractive index, size, composition, and shape.

The force exerted by the scattered beam 8 on the first type of particle is in particular more intense than the force exerted by the scattered beam 8 on the second type of particle.

The particles of the first type 33 will therefore be slowed down, or even trapped, as they cross the region of interaction 18 with the scattered beam 8.

They then reach the collecting means 28 after the predetermined time t1 and, as the valve 30 has been placed in the second position, the particles 33 of the first type exit the valve 30 by the second outlet passage 32.

The particles of the second type 34 reach the collecting means 28 before the predetermined time t1 and, as the valve 30 has been placed in the first position, they exit the valve 30 by the first outlet passage 31.

The device and method therefore perform a sort between particles 33 of a first type and particles 34 of a second type.

Figure 5B:
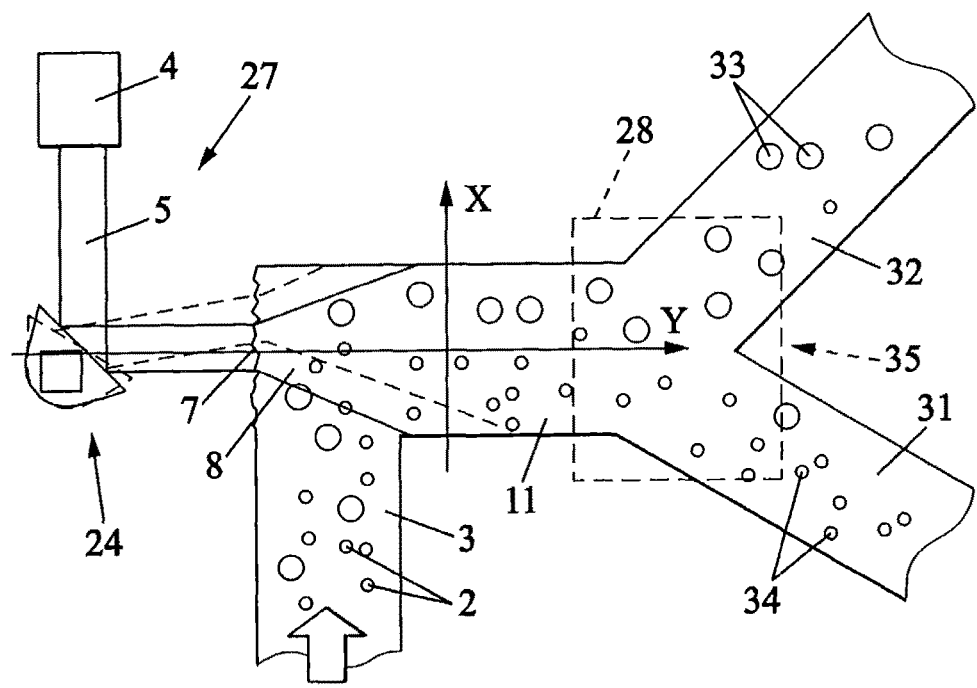
FIG. 5b is a schematic view of a device for sorting particles contained in a fluid according to a second embodiment of the invention.

Referring now to FIG. 5b, another embodiment of a device for sorting 27 particles 2 contained in a fluid 3 may comprise the elements of a device for moving 22 particles 2 contained in a fluid 3 as described above and in particular a means of generating 4 a coherent light beam 5, a passive diffusive element 7 capable of scattering the coherent light beam 5 to yield a scattered beam 8 having an optical speckle field 9, the scattered beam 8 being capable of interacting with a plurality of particles 2 contained in a fluid 3, and a means of moving 24 the optical speckle field 9 of the scattered beam 8.

The device for sorting 27 particles 2 according to the example of FIG. 5b comprises a means of collecting 28 particles to be collected 29 which is formed in a simple manner by a Y-splitter 35 dividing passage 11 into a first outlet passage 31 and a second outlet passage 32.

In this embodiment of a device for sorting 27 particles 2, the means of moving 24 the optical speckle field 9 of the scattered beam 8 allows moving particles 2 in a movement direction X perpendicular to a passage direction Y as already detailed above in relation to the device for moving 22 particles 2.

The plurality of particles 2 here may again comprise at least one particle 33 of a first type and at least one particle 34 of a second type, the first type of particle and the second type of particle differing in their composition or their size.

The force exerted by the scattered beam 8 on the first type of particle is in particular more intense than the force exerted by the scattered beam 8 on the second type of particle, and the movement of particles 33 of the first type along movement direction X will therefore be greater than the movement of particles 34 of the second type.

In this manner, after the interaction region 18 has been crossed, particles 33 of the first type and particles 34 of the second type are no longer located at the same average movement position in passage 11, considered along movement direction X.

When said particles 33, 34 reach the Y-splitter 35 dividing passage 11 into a first outlet passage 31 and a second outlet passage 32, particles 33 of the first type will primarily be collected by the second outlet passage 32 and particles 34 of the second type will primarily be collected by the first outlet passage 31.

The device and method therefore perform a sort between particles 33 of a first type and particles 34 of a second type.

The invention claimed is:

1. A method for trapping particles contained in a fluid in motion,
   the method comprising at least the steps of:
   generating a coherent light beam,
   scattering the coherent light beam by means of a passive diffusive element in order to yield a scattered beam having an optical speckle field with a plurality of areas of constructive interference and destructive interference,
   wherein the passive diffusive element is a rough surface comprising rough areas of dimensions substantially near a wavelength of the coherent light beam,
   trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive or destructive interference, the particles being either:
   dielectric or metal nanoparticles or microparticles,
   or organic nanoparticles or microparticles.

2. The method according to claim 1, wherein the passive diffusive element scatters the coherent light beam into a scattered beam with a speckle contrast ratio substantially greater than fifty percent.

3. The method according to claim 1, wherein the scattering step comprises reflection or transmission of the coherent light beam by the passive diffusive element to yield the scattered beam.

4. The method according to claim 1, wherein the passive diffusive element is a rough internal or external surface of a passage containing the fluid.

5. The method according to claim 1, wherein the particles have an average diameter of between 1 nanometer and 0.1 millimeters.

6. A method for moving particles contained in a fluid, comprising the steps of:
   generating a coherent light beam,
   scattering the coherent light beam by means of a passive diffusive element in order to yield a scattered beam having an optical speckle field with a plurality of areas of constructive interference and destructive interference,
   wherein the passive diffusive element is a rough surface comprising rough areas of dimensions substantially near a wavelength of the coherent light beam,
   trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive or destructive interference, the particles being either:
   dielectric or metal nanoparticles or microparticles,
   or organic nanoparticles or microparticles,
   the method for moving particles further comprising a step of moving particles by modifying the optical speckle field of the scattered beam,
   said step of modifying the optical speckle field of the scattered beam comprises moving the coherent light beam or modifying a wavefront of the coherent light beam before it is scattered to yield a scattered beam.

7. A method for sorting particles contained in a fluid, comprising the steps of
   generating a coherent light beam,
   scattering the coherent light beam by means of a passive diffusive element in order to yield a scattered beam having an optical speckle field with a plurality of areas of constructive interference and destructive interference, wherein the passive diffusive element is a rough surface comprising rough areas of dimensions substantially near a wavelength of the coherent light beam, trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive and destructive interference, the particles being either:

dielectric or metal nanoparticles or microparticles, or organic nanoparticles or microparticles wherein the plurality of particles comprises at least one particle of a first type and at least one particle of a second type, said at least one particle of a first type and said at least one particle of a second type differing in the composition or their size, the method for sorting particles further comprising a step of sorting particles by collecting particles to be collected among the plurality of particles after said particles to be collected have interacted with the scattered beam, wherein the particles to be collected are said at least one particle of the first type.

8. A device for trapping particles contained in a fluid in motion, said device comprising:

a means of generating a coherent light beam, a passive diffusive element configured to scatter the coherent light beam to yield a scattered beam having an optical speckle field with a plurality of areas of constructive and destructive interference, wherein the passive diffusive element is a rough surface comprising rough areas of dimensions substantially near a wavelength of the coherent light beam, the scattered beam is configured to trap particles by interacting with a plurality of particles contained in a fluid in motion so that said plurality of areas of constructive and destructive interference constitutes a plurality of optical traps that exert forces on said particles tending to move said particles toward areas of constructive or destructive interference, the particles being either:

dielectric or metal nanoparticles or microparticles, or organic nanoparticles or microparticles.

9. A device for moving particles contained in a fluid, comprising:

a means of generating a coherent light beam, a passive diffusive element configured to scatter the coherent light beam to yield a scattered beam having an optical speckle field with a plurality of areas of constructive and destructive interference, wherein the passive diffusive element is a rough surface comprising rough areas of dimensions substantially near a wavelength of the coherent light beam, the scattered beam is configured to trap particles by interacting with a plurality of particles contained in a fluid so that said plurality of areas of constructive and destructive interference constitutes a plurality of optical traps that exert forces on said particles tending to move said particles toward areas of constructive or destructive interference, and means of moving particles by modifying the optical speckle field of the scattered beam by moving that coherent light beam or modifying a wavefront of the coherent light beam before it is scattered to yield a scattered beam.

10. A device for sorting particles contained in a fluid, comprising:

a means of generating a coherent light beam, a passive diffusive element configured to scatter the coherent light beam to yield a scattered beam having an optical speckle field with a plurality of areas of constructive interference and destructive interference, wherein in the passive diffusive element is a rough surface comprising rough areas of dimensions substantially near a wavelength of the coherent light beam, the scattered beam is configured to trap particles by interacting with a plurality of particles contained in a fluid so that said plurality of areas of constructive and destructive interference constitutes a plurality of optical traps that exert forces on said particles tending to move said particles toward areas of constructive or destructive interference, wherein the plurality of particles comprises at least one particle of a first type and at least one particle of a second type, said at least one particle of a first type and said at least one particle of a second type differing in their composition or their size, and means of sorting particles by collecting particles to be collected among the plurality of particles after said particles to be collected have interacted with the scattered beam, wherein the particles to be collected are said at least one particle of the first type.

11. A method for trapping particles contained in a fluid in motion, the method comprising at least the steps of:

generating a coherent light beam, scattering the coherent light beam by means of a passive diffusive element in order to yield a scattered beam having an optical speckle field with a plurality of areas of constructive interference and destructive interference, trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive or destructive interference, the particles being either:

dielectric or metal nanoparticles or microparticles, or organic nanoparticles or microparticles, wherein the coherent light beam is generated such that a wavelength of said beam is substantially equal to a wavelength of electromagnetic radiation at which the particles are transparent.

12. The method according to claim 11, wherein the passive diffusive element scatters the coherent light beam into a scattered beam with a speckle contrast ratio substantially greater than fifty percent.

13. The method according to claim 11, wherein the scattering step comprises reflection or transmission of the coherent light beam by the passive diffusive element to yield the scattered beam.

14. The method according to claim 11, wherein the passive diffusive element is a rough internal or external surface of a passage containing the fluid.

15. The method according to claim 11, wherein the particles have an average diameter of between 1 nanometer and 0.1 millimeters.

16. A method for moving particles contained in a fluid, comprising the steps of generating a coherent light beam,
scattering the coherent light beam by means of a passive diffusive element in order to yield a scattered beam having an optical speckle field with a plurality of areas of constructive interference and destructive interference,
trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive or destructive interference, the particles being either:
dielectric or metal nanoparticles or microparticles,
or organic nanoparticles or microparticles,
wherein the coherent light beam is generated such that a wavelength of said beam is substantially equal to a wavelength of electromagnetic radiation at which the particles are transparent,
the method for moving particles further comprising a step of moving particles by modifying the optical speckle field of the scattered beam,
said step of modifying the optical speckle field of the scattered beam comprises moving the coherent light beam or modifying a wavefront of the coherent light beam before it is scattered to yield a scattered beam.

17. A method for sorting particles contained in a fluid, comprising the steps of
generating a coherent light beam,
scattering the coherent light beam by means of a passive diffusive element in order to yield a scattered beam having an optical speckle field with a plurality of areas of constructive interference and destructive interference,
trapping particles by causing the scattered beam to interact with a plurality of particles contained in a fluid in motion so that said plurality of areas of constructive and destructive interference constitutes a plurality of optical traps that exert forces on said particles tending to move said particles toward areas of constructive or destructive interference, the particles being either:
dielectric or metal nanoparticles or microparticles,
or organic nanoparticles or microparticles,
wherein the coherent light beam is generated such that a wavelength of said beam is substantially equal to a wavelength of electromagnetic radiation at which the particles are transparent,
wherein the plurality of particles comprises at least one particle of a first type and at least one particle of a second type, said at least one particle of a first type and said at least one particle of a second type differing in their composition or their size,
the method for sorting particles further comprising a step of sorting particles by collecting particles to be collected among the plurality of particles after said particles to be collected have interacted with the scattered beam,
wherein the particles to be collected are said at least one particle of the first type.

18. A device for trapping particles contained in a fluid in motion, said device comprising:
means for generating a coherent light beam,
a passive diffusive element configured to scatter the coherent light beam to yield a scattered beam having an optical speckle field with a plurality of areas of constructive interference and destructive interference,
the scattered beam configured to trap particles by interacting with a plurality of particles contained in a fluid in motion so that said plurality of areas of constructive and destructive interference constitutes a plurality of optical traps that exert forces on said particles tending to move said particles toward areas of constructive or destructive interference, the particles being either:
dielectric or metal nanoparticles or microparticles, or
organic nanoparticles or microparticles, wherein the coherent light beam is generated such that a wavelength of said beam is substantially equal to a wavelength of electromagnetic radiation at which the particles are transparent.

19. A device for moving particles contained in a fluid, comprising:
means for generating a coherent light beam,
a passive diffusive element configured to scatter the coherent light beam to yield a scattered beam having an optical speckle field with a plurality of areas of constructive interference and destructive interference,
the scattered beam configured to trap particles by interacting with a plurality of particles contained in a fluid so that said plurality of areas of constructive and destructive interference constitutes a plurality of optical traps that exert forces on said particles tending to move said particles toward areas of constructive or destructive interference, wherein the coherent light beam is generated such that a wavelength of said beam is substantially equal to a wavelength of electromagnetic radiation at which the particles are transparent, and
means of moving particles by modifying the optical speckle field of the scattered beam by moving the coherent light beam or modifying a wavefront of the coherent light beam before it is scattered to yield a scattered beam.

20. A device for sorting particles contained in a fluid, comprising:
means for generating a coherent light beam,
a passive diffusive element configured to scatter the coherent light beam to yield a scattered beam having an optical speckle field with a plurality of areas of constructive interference and destructive interference,
the scattered beam configured to trap particles by interacting with a plurality of particles contained in a fluid so that said plurality of areas of constructive and destructive interference constitutes a plurality of optical traps that exert forces on said particles tending to move said particles toward areas of constructive or destructive interference, wherein
the plurality of particles comprises at least one particle of a first type and at least one particle of a second type, said at least one particle of a first type and said at least one particle of a second type differing in their composition or their size,
wherein the coherent light beam is generated such that a wavelength of said beam is substantially equal to a wavelength of electromagnetic radiation at which the particles are transparent, and
means of sorting particles by collecting particles to be collected among the plurality of particles after said particles to be collected have interacted with the scattered beam, wherein the particles to be collected are said at least one particle of the first type.

* * * * *